(12) United States Patent
Alden

(10) Patent No.: US 11,382,766 B2
(45) Date of Patent: Jul. 12, 2022

(54) PROSTHETIC COMPONENT EXTRACTOR

(71) Applicant: Kris Alden, Kinsdale, IL (US)

(72) Inventor: Kris Alden, Kinsdale, IL (US)

( * ) Notice: Subject to any disclaimer, the term of this patent is extended or adjusted under 35 U.S.C. 154(b) by 0 days.

(21) Appl. No.: 16/977,427

(22) PCT Filed: Mar. 1, 2019

(86) PCT No.: PCT/US2019/020437
§ 371 (c)(1),
(2) Date: Sep. 1, 2020

(87) PCT Pub. No.: WO2019/169357
PCT Pub. Date: Sep. 6, 2019

(65) Prior Publication Data
US 2021/0045894 A1  Feb. 18, 2021

Related U.S. Application Data

(60) Provisional application No. 62/637,075, filed on Mar. 1, 2018.

(51) Int. Cl.
*A61F 2/46* (2006.01)
*A61B 17/92* (2006.01)

(52) U.S. Cl.
CPC .......... *A61F 2/4607* (2013.01); *A61B 17/921* (2013.01)

(58) Field of Classification Search
CPC . A61B 17/92; A61B 17/921; A61B 2017/922; A61F 2/4607; A61F 2002/4619
See application file for complete search history.

(56) References Cited

U.S. PATENT DOCUMENTS

| | | | |
|---|---|---|---|
| 2,638,092 A | | 5/1953 | Dorr et al. |
| 3,955,568 A | * | 5/1976 | Neufeld ............... A61F 2/4607 606/86 R |
| 4,253,353 A | * | 3/1981 | Symbol ................ B25B 19/00 81/124.7 |
| 5,409,492 A | * | 4/1995 | Jones .................... A61F 2/4607 606/86 R |
| 8,657,833 B2 | * | 2/2014 | Burgi ................... A61F 2/4607 606/99 |
| 9,089,440 B2 | * | 7/2015 | Mueller ................ A61F 2/461 |
| 9,456,828 B2 | * | 10/2016 | Kerboul ............. A61B 17/1659 |
| 10,092,420 B2 | * | 10/2018 | Kerboul .............. A61F 2/4609 |
| 2005/0240197 A1 | * | 10/2005 | Kmiec ................. A61B 17/921 606/100 |
| 2011/0257656 A1 | * | 10/2011 | Daniels ................ A61F 2/4607 606/99 |
| 2012/0004664 A1 | | 1/2012 | Paul |
| 2014/0207123 A1 | | 7/2014 | Mueller |
| 2017/0367714 A1 | | 12/2017 | McCulloch et al. |

FOREIGN PATENT DOCUMENTS

FR           2742334 A1    6/1997

* cited by examiner

*Primary Examiner* — Anu Ramana

(57) ABSTRACT

The present device described herein is intended to effect the removal of an intramedullary component of an orthopaedic prosthetic implant. The extraction device utilizes a hook which can be secured to the implant, particularly the neck of a femoral prosthetic component. The hook is attached to an elongated member that contains two striking surfaces. A force applied to the striking surface(s) is transmitted to the prosthesis so as to extract the implant from the intramedullary cavity of a bone.

20 Claims, 10 Drawing Sheets

Fig. 4A
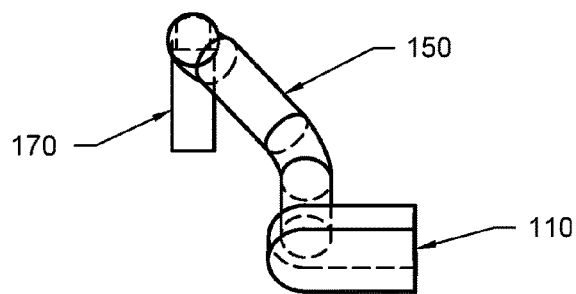
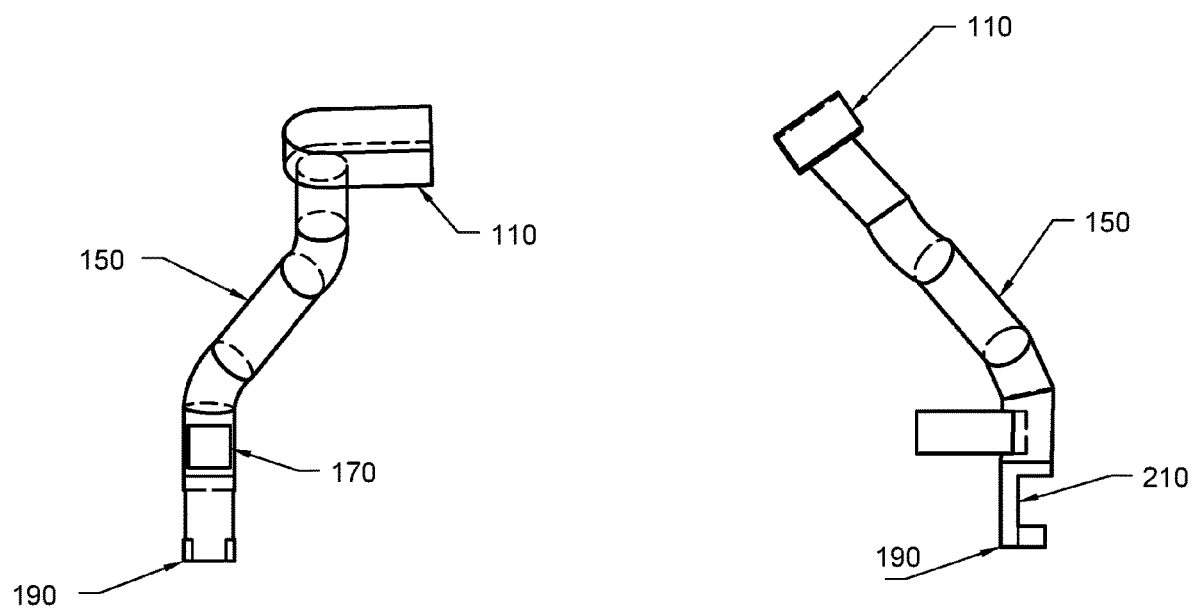
Fig. 4B
Fig. 4C

Fig. 5B
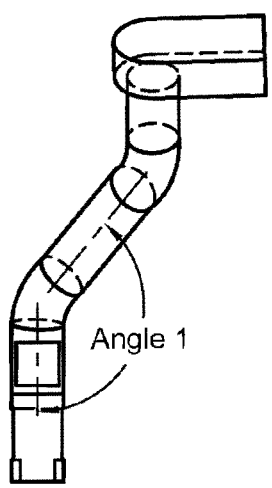
Fig. 5C
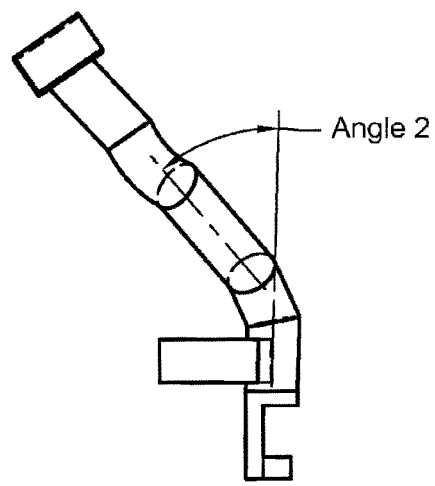
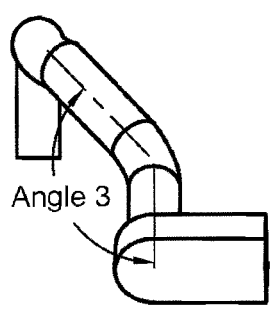
Fig. 5A
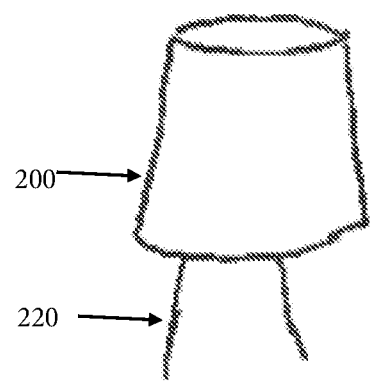
Fig. 6

PROSTHETIC COMPONENT EXTRACTOR

CROSS-REFERENCE TO RELATED APPLICATIONS

This application is a § 371 national phase entry of International Application No. PCT/US2019/020437, filed Mar. 1, 2019, which claims priority to U.S. Provisional Patent Application No. 62/637,075, filed Mar. 1, 2018, the entirety of which is incorporated herein by reference.

FIELD OF THE INVENTION

The present disclosure relates to devices for extracting artificial joints, implants, or orthopedic prosthetics from the intramedullary cavity of a bone.

SUMMARY OF THE RELATED ART

Unless otherwise indicated herein, the materials described in this section are not admitted to be prior art to the claims in this application.

Load-carrying joints, such as the hip, can be rendered painful and thereby nonfunctional due to a multitude of disease states such as arthritis, fracture, or congenital deformity. The end result of the various pathophysiologic processes that impact a joint include degeneration, resulting in pain and loss of function for the individual. Joint replacement procedures with prosthetic implants have successfully treated and resolved numerous conditions that result in degeneration of affected joints. Due to both an aging population and younger patients desiring a more active lifestyle not impaired by degenerative conditions, joint replacement surgeries are becoming increasingly common.

In traditional procedures, implants can be affixed to the bone in one of two ways: (i) through cementing the implant into place, or (ii) through biologic fixation after impacting the implant into the medullary cavity of the bone. The un-cemented implants achieve bone ingrowth and integration onto the surface of the implant thereby obtaining biologic fixation. Knee, hip, and shoulder replacement procedures are the most commonly performed joint replacements worldwide. Hip implants, in particular, include an acetabular component, which is affixed to the pelvis, and a femoral component, which is secured to the proximal femur. The femoral component accepts a head component that articulates in a liner which is secured into the acetabular component.

The widespread adoption of orthopaedic implants to ameliorate degenerative joint conditions also has an important corollary: a variable percentage of prosthetic implants will ultimately fail. These prosthetic failures are due to a variety of etiologies including implant loosening, infection, dislocation, instability, and periprosthetic fracture. The failed implants must be removed during revision joint replacement procedures, whereby revision prosthetics allow for pain relief, mobility, and enhance the function of the individual. The current methodologies and tools available for the removal of prosthetics are generally rudimentary and have not evolved to facilitate modern and less invasive surgical techniques. The presently available implant removal tools require longer operative times, enlarged surgical dissection and incisions, and have less favorable success rates.

The bond that retains the component in the bone (either cement or biologic fixation) must be broken to facilitate removal of the failed implant. Should the current tools fail to achieve removal of the implant, surgical techniques to affect prosthetic removal include cutting the bone, i.e., performing an osteotomy. The revision joint replacement procedures that require an osteotomy are more invasive, of longer duration, require osteotomy healing, and significantly prolong recovery time for the patient. The physical work to remove well-fixed implants during a revision type surgical procedure can result in muscle, tissue, and bone damage, and thereby require longer operative times, reduce native host bone stock, increase the risk of postoperative surgical complications, and require longer patient recovery periods.

Commonly used surgical disimpaction techniques typically begin with the use of osteotomes to initially break the proximal bond between the implant and the host bone. This procedure and the instrumentation are generally limited in both the scope and depth of penetration. Once the maximal safe depth of penetration into the host bone is attained, further extraction techniques are required. Retrograde disimpaction of a femoral component through the employment of bone tamps can be used, but such a procedure is predicated on the implant having a collar or reasonable striking surface to impact and thereby dislodge the component. In addition, retrograde disimpaction may also require excessive bone removal and is generally ineffective due to the significant loss of force operating through an inferior angle through which the surgeon must direct force. Antegrade removal of a prosthetic implant is thereby the generally preferred surgical technique. Several modern prosthetic implants have a screw hole in the shoulder of the implant that can be used to affix an extraction device. However, these screw holes are generally inaccessible during the extraction phase of the revision joint replacement procedure and, therefore, are rarely helpful to effect extraction.

Attaching an extraction instrument to the trunion of the femoral implant is a more facile approach to effect surgical removal. Such methods generally employ fixing an extractor to the proximal part of the prosthetic implant with pliers (or a similar instrument) and striking the instrument. Additionally, using a slaphammer device affixed to the implant to backslap the implant out of the bone can also be utilized. These devices are bulky, difficult to use, require greater surgical dissection, and generally do not permit the operator to generate sufficient force to break the bond between the implant and the host bone and thereby extract the implant.

SUMMARY

In view of the foregoing, it may be recognized that the above devices and methods are generally and practically ineffective in transmitting sufficient force to break the remaining bond between the implant and bone to thereby extract the prosthesis. Naturally, the force required to remove the implant must be less than the force that fixes the extractor to the implant, i.e. the fixation strength of the extractor to the implant must be greater than the force require to remove it. In the common scenario where the force required to remove the implant is greater than that achieved by the extractor, the extractor will ultimately fail to transmit sufficient force to the implant to effect its removal from the host bone. Therefore, a more facile, less invasive mechanism to exert force on the implant and thereby effect prosthetic implant removal may be desired.

Thus, in one embodiment, a device is provided. The device includes an elongated member having a first end and a second end, the elongated member comprising substantially straight, rod-like first, second, and third segments each having first and second ends, the first and second segments being connected by a first curved segment at their second and first ends, respectively, and the second and third segments being connected by a second curved segment at their second and first ends, respectively, and the first ends of each of the segments are proximal to the first end of the elongated member relative to the second ends of the segments. The device also includes a first striking surface positioned on the first segment extending away from the elongated member. The device also includes a second striking surface positioned on the third segment extending away from the elongated member. The device also includes a hook positioned at the second end of the third segment, wherein the hook includes a channel substantially perpendicular to a long axis of the third segment that is configured to engage a surgical implant.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIGS. 4A-4C illustrates the front view, the right side view, and the top view of the example device of FIG. 1, respectively, according to an example embodiment.

FIGS. 5A-5C illustrate the front view, the right side view, and the top view of the example device of FIG. 1, respectively, including angles between the various components, according to an example embodiment.

FIG. 6 illustrates an example implant for extraction using the device of FIG. 1, according to an example embodiment.

DETAILED DESCRIPTION

Figure 1:
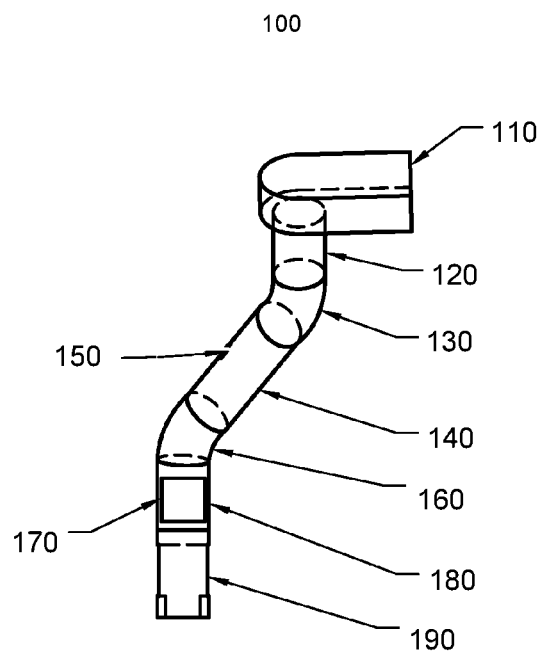
FIG. 1 illustrates a front view of an example device for a left hip, according to an example embodiment.
Figure 2:
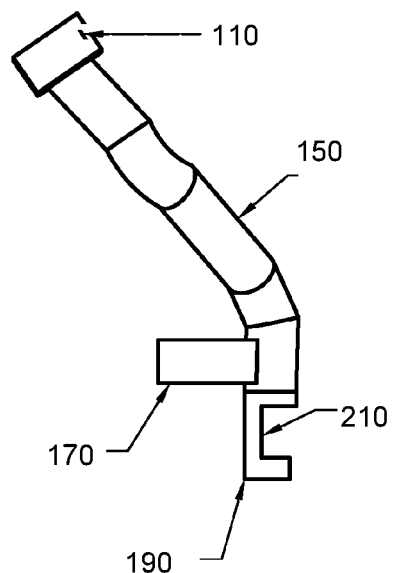
FIG. 2 illustrates a right side view of the example device for a left hip of FIG. 1, according to an example embodiment.
Figure 3:
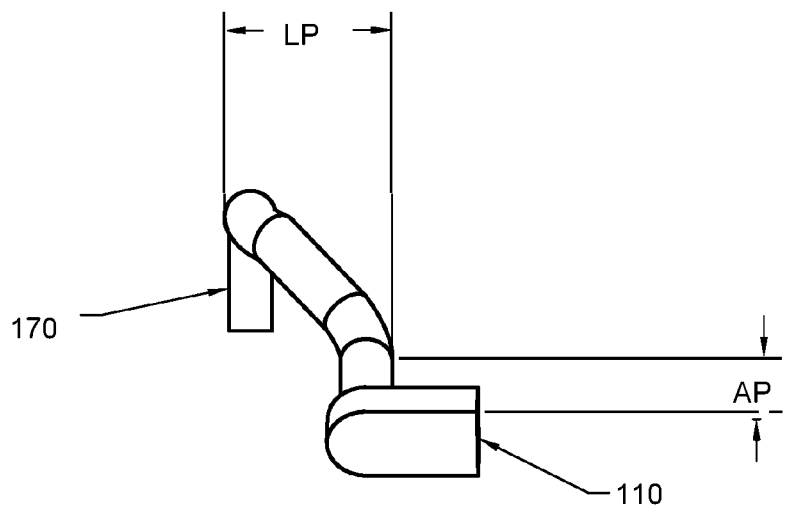
FIG. 3 illustrates a top view of the example device for a left hip of FIG. 1, according to an example embodiment.

Exemplary devices and systems are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" and "substantially" each means+/−5%.

As used herein, "coupled" means associated directly as well as indirectly. For example, a member A may be directly associated with a member B, or may be indirectly associated therewith, e.g., via another member C.

In the following description, numerous specific details are set forth to provide a thorough understanding of the disclosed concepts, which may be practiced without some or all of these particulars. In other instances, details of known devices and/or processes have been omitted to avoid unnecessarily complicating and obscuring the disclosure. While some concepts will be described in conjunction with specific examples, it will be understood that these examples are not intended to be limiting.

Unless otherwise indicated, the terms "first," "second," etc. are used herein merely as labels and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The present disclosure describes a prosthetic implant extraction device 100 to facilitate the surgical removal of a femoral component 270 of hip joint implant or intramedullary orthopaedic implant (cemented or uncemented intramedullary orthopaedic implants). The extractor device 100 described herein facilitates, tolerates, and transfers the high kinetic energy expended by the operator to the implant to disrupt the implant/bone interface and thereby affect the removal of the prosthetic component. In addition, the extractor device 100 is predicated on less invasive surgical techniques and exposure to minimize tissue and bone damage and optimize revision joint replacement procedures. As such, the present invention provides a more effective means to extract an implanted prosthetic component from the intramedullary canal. The overall goal achieved by the present invention is an efficient, less invasive, and facile means for extract an orthopaedic implant with a minimal amount of time, physical effort, and host tissue and bone damage.

In particular, the present disclosure provides a device 100 comprising (a) an elongated member 150 having a first end and a second end, the elongated member comprising substantially straight, rod-like first 120, second 140, and third 180 segments each having first and second ends, the first 120 and second 140 segments being connected by a first curved segment 130 at their second and first ends, respectively, and the second 140 and third 180 segments being connected by a second curved segment 160 at their second and first ends, respectively, and the first ends of each of the segments 120, 140 and 180 are proximal to the first end of the elongated member 150 relative to the second ends of the segments, (b) a first striking surface 110 positioned on the first segment 120 extending away from the elongated member 150, (c) a second striking surface 170 positioned on the third segment 180 extending away from the elongated member 150, and (d) a hook 190 positioned at the second end of the third segment 180, wherein the hook 190 includes a channel 210 substantially perpendicular to a long axis of the third segment 180 that is configured to engage a surgical implant.

Figure 7A:
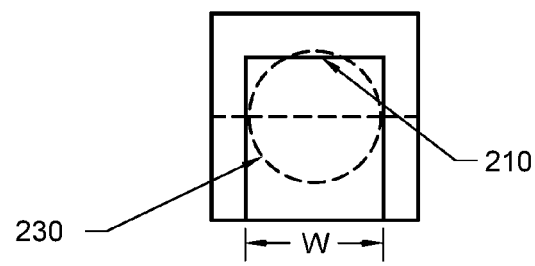
FIG. 7A illustrates a bottom view of a hook of the device of FIG. 1, according to an example embodiment.
Figure 7B:
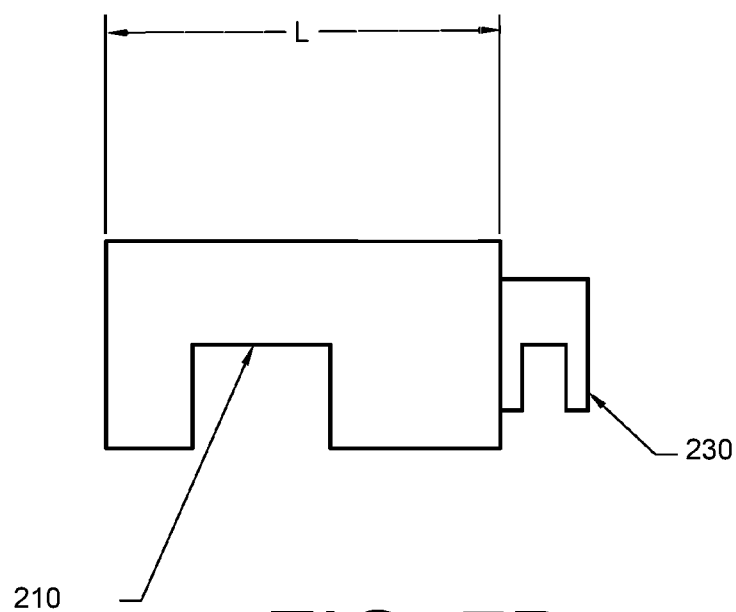
FIG. 7B illustrates a side view of the hook of FIG. 6A, according to an example embodiment.
Figure 8:
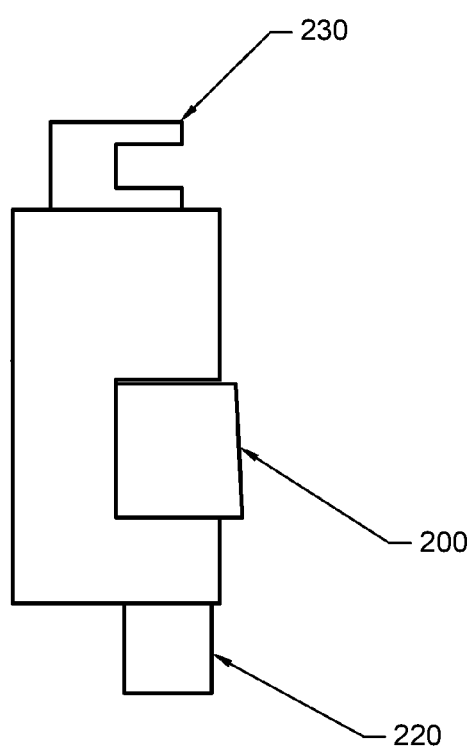
FIG. 8 illustrates a side view of the hook and lock of FIGS. 7A and 7B, according to an example embodiment.
Figure 9B:
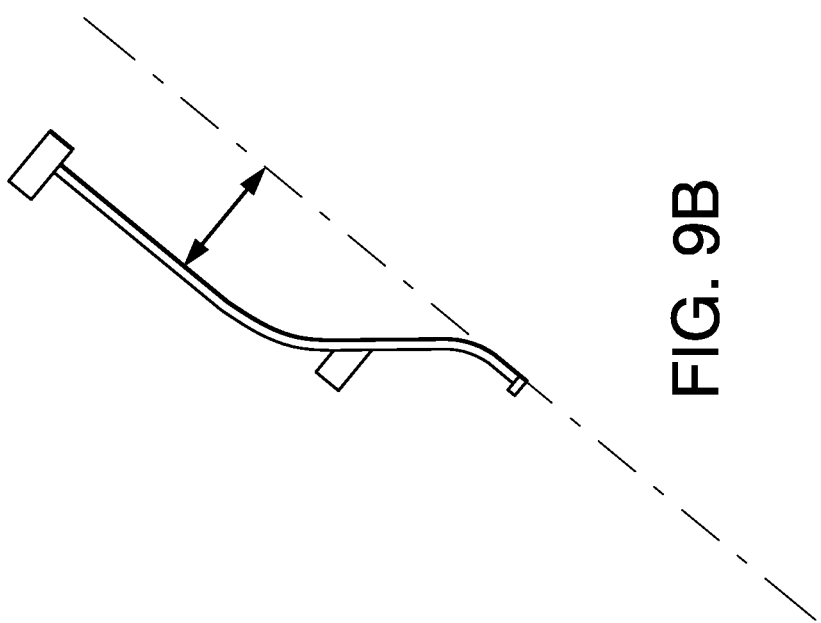
FIG. 9B illustrates a side view of another example device demonstrating the offset in the anterior plane, according to an example embodiment.
Figure 9A:
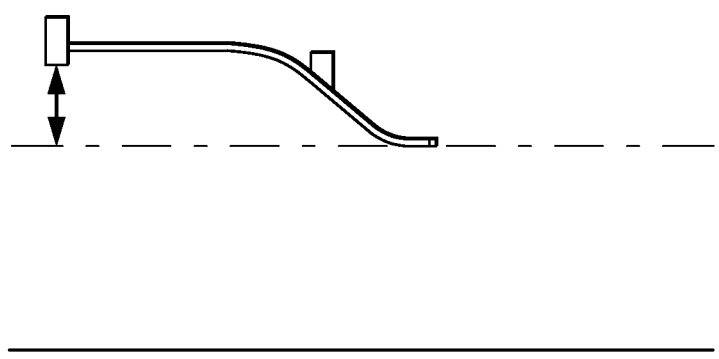
FIG. 9A illustrates a top view of another example device demonstrating the offset in the lateral plane, according to an example embodiment.
Figure 10:
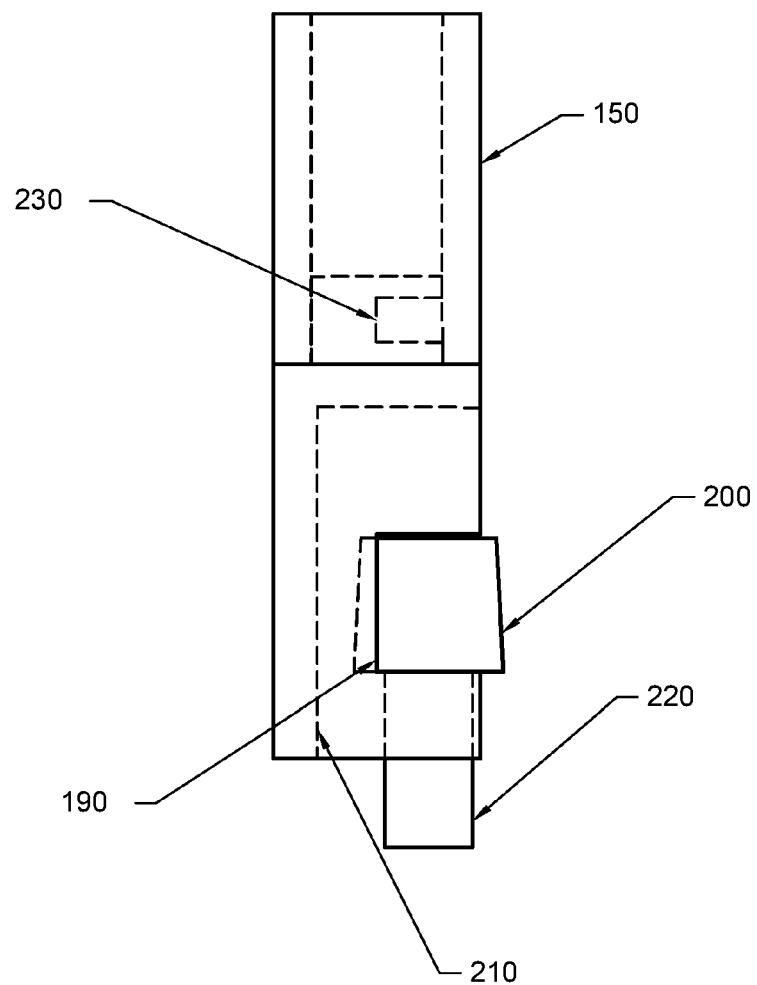
FIG. 10 illustrates a side view of the hook and lock, according to an example embodiment.
Figure 11:
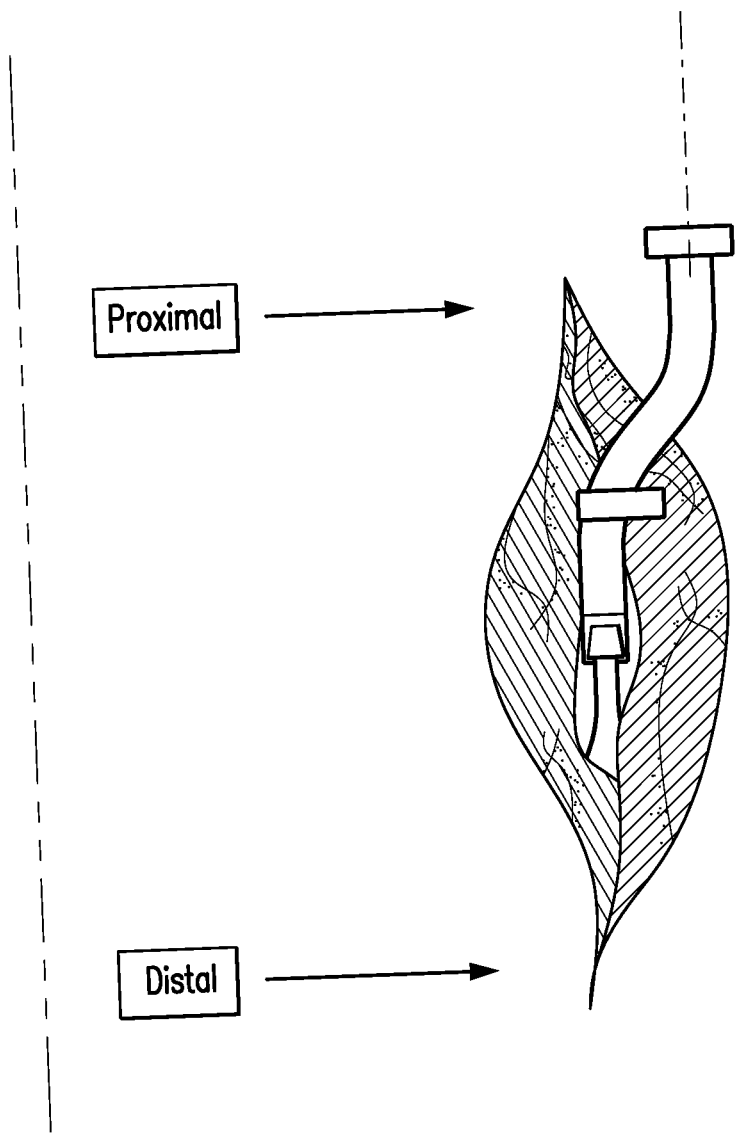
FIG. 11 illustrates a top view of the elongated member engaged with the hook and lock as it secures onto the trunnion of the femoral component, according to an example embodiment.
Figure 12:
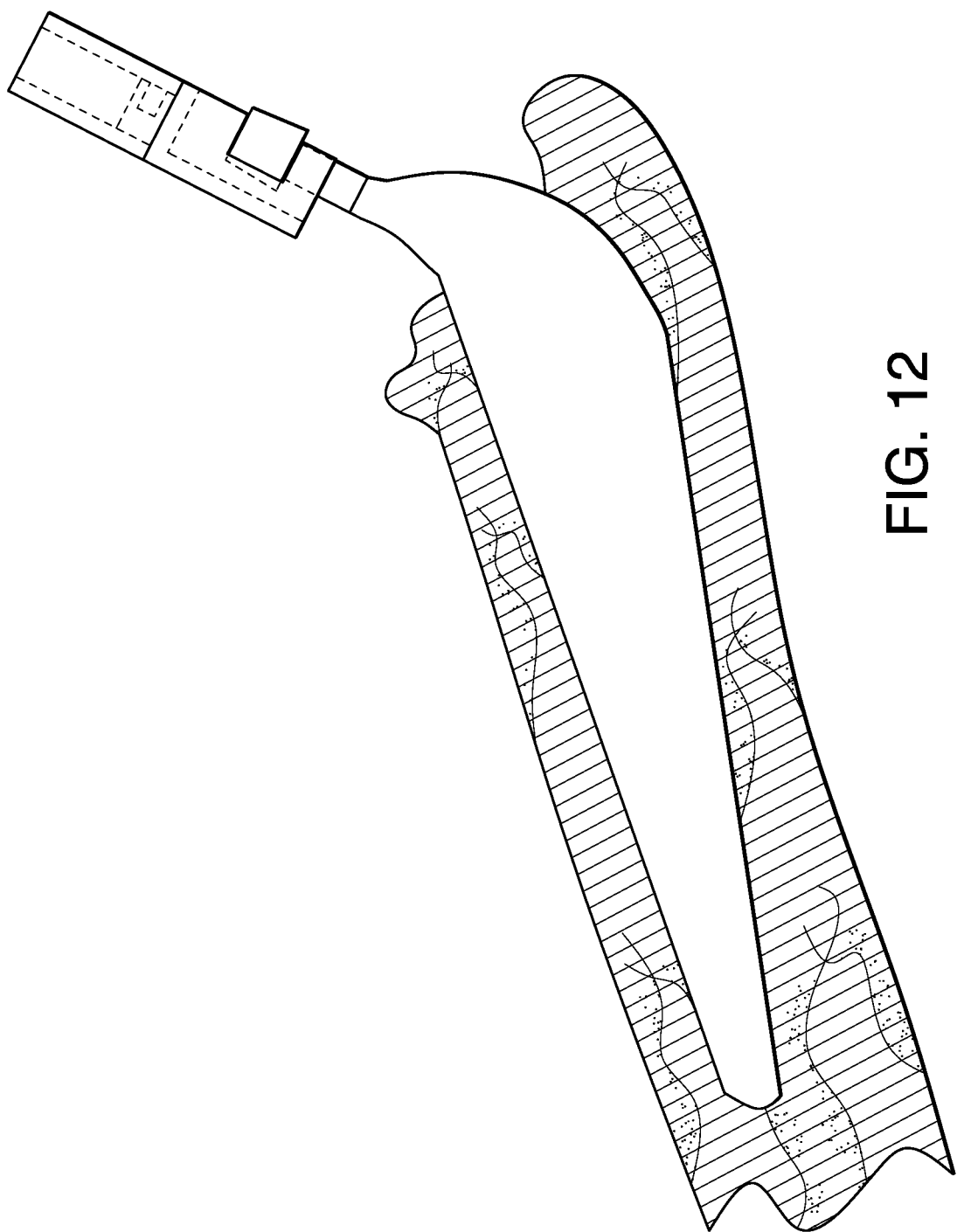
FIG. 12 illustrates a side view of the elongated member engaged with the hook and lock as it secures onto the trunnion of the femoral component, according to an example embodiment.
Figure 13:
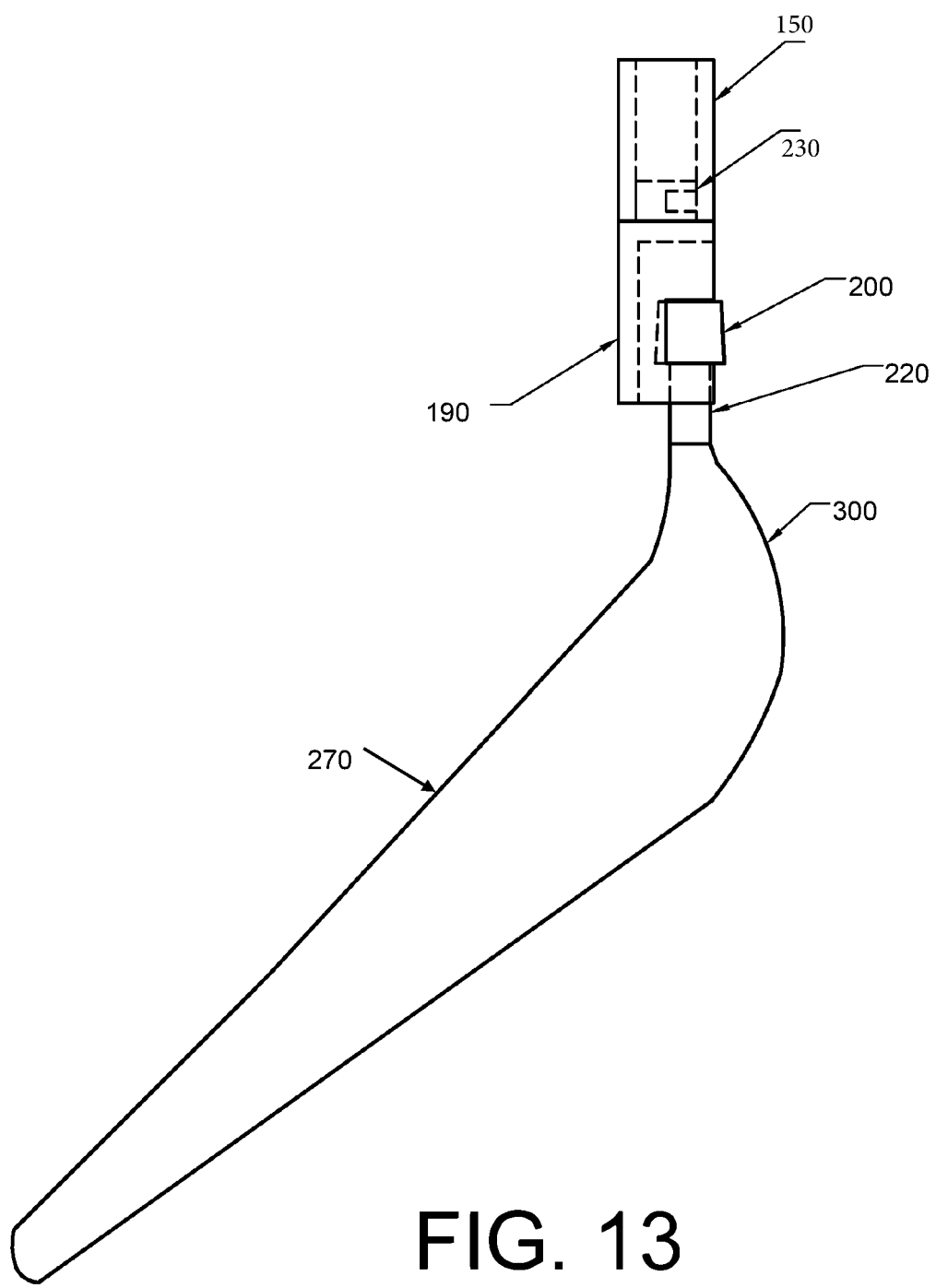
FIG. 13 illustrates a side view of the hook prior to engagement onto the trunnion of the femoral component and after engagement of the hook onto the trunnion, according to an example embodiment.

The hook 190 may be integrated into the second end of the third segment or modular and variably sized such that it can be secured to the neck 220 of the implant distal to the implant neck 220 or trunnion 200. Each such hook 190 may be configured for attachment to a specific stem implant having a known shape, size and geometry. The hook 190 may have a length (L) ranging from about 2 cm to about 4 cm. The length (L) of the hook is measured from a centerline extending into the hook starting at the proximal end (the end adjacent to the elongated member) and continuing to the distal end. As such, the length (L) of the hook is measured in a direction parallel to the long axis of the third segment 180 of the elongated member 150, as shown in FIGS. 1 and 7B. The variable sizes are optimized to a specific prosthesis and configured to be smaller than the trunnion section of the implant but larger than the neck of the prosthesis to provide for a secure mechanical coupling and grip of the proximal implant. In another embodiment, the hook channel width (W) is adjustable for engaging a specific prosthesis. In one embodiment, the channel is U-shaped such that a side of the hook is open to receive the neck of the prosthesis. In some embodiments, the channel of the hook may have a width (W) ranging from about 2 cm to about 3 cm. The width (W) is measured from a first interior surface of the channel to a second interior surface of the channel in a direction perpendicular to the long axis of the third segment of the elongated member, as shown in FIGS. 1 and 7A.

In one example, the hook 190 is permanently affixed to the second end of the elongated member 150. In another example, the hook 190 is removably coupled to the second end of the elongated member 150. In such embodiments, the device may include a lock 230 between the second end of the elongated member 150 and the hook 190. Preferably the lock 230 connects the hook 190 to the second end of the elongated member 150 such that there is little or no play between the two components. In one particular example, the hook 190 may include a clip, and the second end of the elongated member 150 may include a lever configured to mate with the clip to thereby removably couple the hook to the elongated member. Other mechanisms for removably coupling the hook to the elongated member are possible as well.

In one embodiment, the elongated member is offset in an anterior plane "AP" and further offset in a lateral plane "LP". As used herein, the "anterior plane" indicates a plane that is anterior to the ventral surface of the patient, e.g. ventral to the coronal midaxis of the patient's body. As used herein, the "lateral plane" indicates a plane lateral to the sagittal plane of the patient, e.g. lateral to the sagittal midaxis of the patient's body. The anterior offset and lateral offset are in essence in perpendicular planes to each other.

The elongated member transitions at an optimal angle to permit both the transmission of force to the implant and for its use in less invasive surgical procedures. In particular, the elongated member is offset in the anterior plane between about 30 degrees and about 50 degrees, and the elongated member is offset in the lateral plane between about 40 degrees and about 60 degrees. Offset in the anterior plane refers to an angled deviation from the mid-ventral surface of the patient in the coronal plane and offset in the lateral plane refers to an angled deviation from the midline axis of the patient in the sagittal plane, as illustrated in FIGS. 1-4.

In one example, as shown in FIG. 1, the elongated member 150 comprises a first segment 120, a second segment 140, and a third segment 180. The first segment 120 is positioned at the first end of the elongated member 150, the third segment 180 is positioned at the second end of the elongated member 150, and the second segment 140 is positioned between the first segment 120 and the third segment 180. In such an example, the first, second, and third segments are substantially straight and rod-like. The first segment has a length ranging from about 4 cm to about 6 cm, the second segment has a length ranging from about 5 cm to about 7 cm, and the third segment has a length ranging from about 5 cm to about 7 cm. In one example, each of the first, second, and third segments have different lengths. In another example, each of the first, second, and third segments have the same lengths. In another example, the first and second segments have the same length, while the third segment has a different length. In another example, the first and third segments have the same length, while the second segment has a different length. In yet another example, the second and third segments have the same length, while the first segment has a different length.

The cross-sections of the segments 120, 140, 180 can be any convenient shape, such as round, elliptical, square, or rectangular, but typically they will be round. The first segment has a diameter ranging from about 2 cm to about 4 cm, the second segment has a diameter ranging from about 2 cm to about 4 cm, and the third segment has a diameter ranging from about 2 cm to about 4 cm. In one example, each of the first, second, and third segments have different diameters. In another example, each of the first, second, and third segments have the same diameters. In another example, the first and second segments have the same diameter, while the third segment has a different diameter. In another example, the first and third segments have the same diameter, while the second segment has a different diameter. In yet another example, the second and third segments have the same diameter, while the first segment has a different diameter. When the cross-sections are shaped differently than a circle their general size will be the same as described above.

As shown in FIG. 1, the first 120 and second 140 segments are connected by a first curved segment 130 at their second and first ends, respectively, and the second 140 and third 180 segments being connected by a second curved segment 160 at their second and first ends, respectively. As used herein, "curved" means a segment that is bent at an angle or, more frequently, has a continuously bending centerline. The first 130 and second 160 curved sections provide an offset in an anterior plane and a further offset in a lateral plane. In particular, as shown in FIG. 4, the long axes of the second and third segments are located in a first plane. The angle between the long axis of the third segment and the long axis of the second segment (labeled angle 1 in FIG. 5B) may range from between about 40 degrees and about 60 degrees, which represents an offset in the lateral plane. The first and second segments are located in a second plane that is different than the first plane. The first segment has an angle ranging between about 30 degrees and about 50 degrees with respect to the long axis of the third segment (labeled angle 2 in FIG. 5C) and an angle ranging between about 40 degrees and about 100 degrees with respect to an axis in the first plane that is perpendicular to the long axis of the third segment.

In one particular example, the second segment 140 curves in a direction away from the anterior plane and a direction away from the lateral plane. In one example, the first striking surface 110 extends away from the first segment 120 of the elongated member 150 in a direction substantially perpendicular to the long axis of the first segment 120 and away from the midline axis "M" of the patient as shown in FIG. 1, and the second striking surface 170 extends away from the third segment 180 of the elongated member 150 in a direction substantially perpendicular to the long axis of the third segment 180 and away from the channel 210 in the lock 230. In another example, the first striking surface 110 extends away from the first segment 120 of the elongated member 150 in a direction substantially perpendicular to the long axis of the first segment 120 and away from the midline axis "M" of the patient as shown in FIG. 1, and the second striking surface 170 extends away from the second segment 140 of the elongated member 150 in a direction substantially perpendicular to the long axis of the third segment 180 and away from the channel 210 in the lock 230. Other arrangements are possible as well.

In one example, the device may comprise a kit including two elongated members, one left and one right. Only one elongated member is coupled to the lock at a given time. The left and right elongated members may be mirror images of one another. The left elongated member would be used to extract a femoral implant positioned in the left hip of a patient, while the right elongated member would be used to extract a femoral implant positioned in the right hip of the patient. In one example, the kit does not include the lock. In another example, the kit includes a single lock. Only one elongated member is coupled to the lock at a given time. The lock may be decoupled from the right elongated member and coupled to the left elongated member when a medical professional extracts a femoral implant positioned in the left hip of a patient. In another example, each of the left and right elongated members includes its own lock as part of the kit.

As discussed above, the elongated member 150 may further include two striking surfaces 110, 170 extending away from the elongated member. In one example, the length of the first striking surface 110 is equal to the length of the second striking surface 170. The length of the first striking surface is measured from a first end to a second end of the first striking surface along a long axis of the first striking surface, and the length of the second striking surface is as measured from a first end to a second end of the second striking surface along a long axis of the second striking surface. In another example, the length of the second striking surface is greater than the length of the second striking surface. The elongated member 150 may have a length ranging from about 15 cm to about 25 cm. As used herein, the length of the elongated member comprises the arc length, or the length of the centerline of the elongated member, from the first end to the second end. The first striking surface 110 may have a length ranging from about 1 cm to about 2 cm, and the second striking surface 170 may have a length ranging from about 7 cm to about 9 cm.

Generally, the first 110 and second 170 striking surfaces comprise a protrusion capable of transferring the force from the impact of a hammer strike to the elongated member 150. More particularly, the first and second striking surfaces comprise a protrusion from the elongated member, preferably principally in a direction perpendicular to a longitudinal line or tangent to a generally longitudinal arc along the length of the hook 190 at the location of the protrusion. In particular, the first striking surface 110 extends away from a long axis of the first segment 120 in a substantially perpendicular direction to the long axis of the first segment 120 at the point at which the first striking surface 110 is positioned, and the second striking surface 170 extends away from a long axis of the third segment 180 in a substantially perpendicular direction to the long axis of the third segment 180 at the point at which the second striking surface 170 is positioned. As such, the long axes of the first and second striking surfaces may be substantially parallel to one another. The first and second striking surfaces can be rounded or comprise a flat surface for receiving hammer strikes. The longitudinal direction of the first and second striking surfaces extends in a direction away from the anterior plane.

The first 110 and second 170 striking surfaces on the elongated member 150 are designed to tolerate and transfer the impact of a strike (e.g., a hammer strike) by the operator and transmit the force to disrupt the prosthetic/bone interface. In one example, the first striking surface may be positioned between the first end of the elongated member and the second striking surface. In another example, the first striking surface may be positioned at the first end of the elongated member. The first striking surface is generally positioned near the first end of the elongated member (e.g., within 5 cm of the first end of the elongated member). The second striking surface may be positioned at the first end of the third segment of the elongated member. As shown in FIG. 1, the second striking surface may be positioned near the second curved segment 160 of the elongated member. The materials that make up the device, including the elongated member 150, the first 110 and second 170 striking surfaces, and the hook 190, would be corrosion resistant stainless steel typical of orthopedic devices, or other metal alloys that allow for sterilization without significant deformation.

The foregoing describes an implant extractor device 100 to facilitate the removal of a femoral component 270 of a hip joint prosthesis, as one particular non-limiting example. Femoral implants 270 have a trunnion 200, neck 220, and shoulder 300 region which are proximal to the stem that is implanted into the proximal medullar cavity of the femur 310. The device described herein may be secured to the stem at the junction of the trunnion 200 and the neck 220 of the implant. The hook contains a channel of sufficient size to receive the neck of the implant, but small enough to deny passage of the trunnion through it. As such, the hook takes advantage of the differential between the size of the trunnion and the size of the neck of the implant. Due to the varying sizes of implant necks, multiple sizes of the hooks would be necessary, hence the modularity and/or adjustability of the hook. In addition, the hook is secured to the elongated member, which is offset in two planes, anteriorly and laterally, permitting the application of the device in an easy, secure, and less invasive manner. The force generated by the operator will then be transmitted efficiently to the implant via the device so as to effect the prosthetic removal.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

What is claimed is:

1. A device comprising:
   an elongated member having a first end and a second end, the elongated member comprising substantially straight, rod-like first, second, and third segments each having first and second ends, the first and second segments being connected by a first curved segment at their second and first ends, respectively, and the second and third segments being connected by a second curved segment at their second and first ends, respectively, and the first ends of each of the segments are proximal to the first end of the elongated member relative to the second ends of the segments;
   a first striking surface positioned on the first segment extending away from the elongated member;
   a second striking surface positioned on the third segment as a protrusion extending away from the elongated member; and
   a hook positioned at the second end of the third segment, wherein the hook includes a channel that is oriented substantially perpendicular to a long axis of the third segment and wherein the hook is configured to engage a surgical implant.

2. The device of claim 1, wherein the channel is u-shaped such that a side of the hook is open.

3. The device of claim 1, wherein a length of the first striking surface as measured from a first end to a second end of the first striking surface along a long axis of the first striking surface is equal to a length of the second striking surface as measured from a first end to a second end of the second striking surface along a long axis of the second striking surface.

4. The device of claim 1, wherein a length of the second striking surface as measured from a first end to a second end of the second striking surface along a long axis of the second striking surface is greater than a length of the first striking surface as measured from a first end to a second end of the first striking surface along a long axis of the first striking surface.

5. The device of claim 1, wherein the elongated member is offset in an anterior plane and further offset in a lateral plane.

6. The device of claim 5, wherein an angle between a long axis of the first segment and the long axis of the third segment ranges from about 30 degrees to about 50 degrees, and wherein an angle between the long axis of the third segment and a long axis of the second segment ranges from about 40 degrees to about 60 degrees.

7. The device of claim 1, wherein a long axis of the elongated member extending through the center of the elongated member from the first end to the second end has a length ranging from about 15 cm to about 25 cm.

8. The device of claim 1, wherein the channel has a width in a direction perpendicular to the long axis of the third segment ranging from about 2 cm to about 3 cm.

9. The device of claim 1, wherein the hook has a length in a direction parallel to the long axis of the third segment ranging from about 2 cm to about 4 cm.

10. The device of claim 1, wherein the first striking surface has a length ranging from about 1 cm to about 2 cm as measured from a first end to a second end of the first striking surface along a long axis of the first striking surface, and wherein the second striking surface has a length ranging from about 7 cm to about 9 cm as measured from a first end to a second end of the second striking surface along a long axis of the second striking surface.

11. The device of claim 1, wherein the channel is sized such that it has a width that is smaller than a trunnion section of the surgical implant but larger than a neck of the surgical implant to thereby provide a secure mechanical coupling to the surgical implant.

12. The device of claim 1, wherein the hook is adjustable to change a width of the channel.

13. The device of claim 1, further comprising a lock between the second end of the elongated member and the hook such that the hook is removably coupled to the second end of the elongated member.

14. The device of claim 13, wherein the lock comprises a clip on the hook, and wherein the second end of the elongated member includes a lever configured to mate with the clip to thereby removably couple the hook to the elongated member.

15. The device of claim 1, wherein the device includes a plurality of interchangeable hooks, each hook being configured for attachment to a specific surgical implant having a known shape, size and geometry.

16. The device of claim 1, wherein the first striking surface is positioned between the first end of the elongated member and the second striking surface.

17. The device of claim 1, wherein the first striking surface is positioned at the first end of the elongated member.

18. The device of claim 1, wherein the second striking surface is positioned at the first end of the third segment.

19. The device of claim 1, wherein the first striking surface extends away from a long axis of the first segment in a substantially perpendicular direction to the long axis of the first segment, and wherein the second striking surface extends away from a long axis of the third segment in a substantially perpendicular direction to the long axis of the third segment.

20. The device of claim 1, wherein the first segment has a length ranging from about 4 cm to about 6 cm, wherein the second segment has a length ranging from about 5 cm to about 7 cm, and wherein the third segment has a length ranging from about 5 cm to about 7 cm.

* * * * *